(12) United States Patent
Rosow et al.

(10) Patent No.: US 7,774,215 B2
(45) Date of Patent: Aug. 10, 2010

(54) ENTERPRISE-WIDE HOSPITAL BED MANAGEMENT DASHBOARD SYSTEM

(75) Inventors: Eric Rosow, Avon, CT (US); Joe Adam, West Hartford, CT (US); Chris Roth, West Hartford, CT (US)

(73) Assignee: Eclipsys Corporation, Irvine, CA (US)

( * ) Notice: Subject to any disclaimer, the term of this patent is extended or adjusted under 35 U.S.C. 154(b) by 0 days.

(21) Appl. No.: 12/119,664

(22) Filed: May 13, 2008

(65) Prior Publication Data

US 2008/0221926 A1 Sep. 11, 2008
US 2009/0119127 A1 May 7, 2009

Related U.S. Application Data

(63) Continuation of application No. 10/238,427, filed on Sep. 9, 2002.

(60) Provisional application No. 60/317,784, filed on Sep. 7, 2001.

(51) Int. Cl.
*G06Q 10/00* (2006.01)
*G06Q 50/00* (2006.01)

(52) U.S. Cl. ........................ 705/2; 705/3; 705/4; 705/1; 340/5.53; 340/925.49; 600/300

(58) Field of Classification Search ................ 705/2–4; 340/5.54, 925; 600/300
See application file for complete search history.

(56) References Cited

U.S. PATENT DOCUMENTS

| | | | |
|---|---|---|---|
| 4,135,241 A | 1/1979 | Stanis |
| 4,807,155 A | 2/1989 | Cree et al. |
| 5,065,315 A | 11/1991 | Garcia |
| 5,463,546 A | 10/1995 | Parkhurst |
| 5,475,364 A | 12/1995 | Kenet |
| 5,533,183 A | 7/1996 | Henderson, Jr. et al. |
| 5,581,461 A | 12/1996 | Coll et al. |
| 5,809,477 A | 9/1998 | Pollack |
| 5,909,668 A | 6/1999 | Fukuma |
| 5,991,730 A | 11/1999 | Lubin et al. |
| 5,999,208 A | 12/1999 | McNerney et al. |
| 6,047,259 A | 4/2000 | Campbell et al. |
| 6,079,863 A | 6/2000 | Furukawa et al. |

(Continued)

OTHER PUBLICATIONS

Information Disclosure Statement (IDS) Letter Regarding Common Patent Application(s), submitted by Applicant on Dec. 28, 2008.

*Primary Examiner*—Gerald J. O'Connor
*Assistant Examiner*—Linh-Giang Michelle Le
(74) *Attorney, Agent, or Firm*—Tillman Wright, PLLC; Chad D. Tillman; Jeremy C. Doerre

(57) ABSTRACT

An integrated health care delivery network with enabling software and network technology to maximize bed resources, manage varying census levels, and avoid patient diversions through real-time monitoring, automation and communication, is disclosed. Preferably, the present invention is embodied in a bed management/census control dashboard (BMD) system that interfaces with and complements existing Admission/Discharge/Transfer (ADT) systems. The BMD system is an easy-to-use business intelligence application that is designed to allow administrators, clinicians and managers to easily access, analyze and display real-time patient and bed availability information from ancillary information systems, databases and spreadsheets. It enables users to see trends and relationships in hospital (bed) management data directly from their desktop personal computers.

30 Claims, 6 Drawing Sheets

U.S. PATENT DOCUMENTS

| | | |
|---|---|---|
| 6,101,534 A * | 8/2000 | Rothschild ................ 709/217 |
| 6,163,903 A | 12/2000 | Weismiller |
| 6,356,874 B1 | 3/2002 | Ohrn |
| 6,362,725 B1 | 3/2002 | Ulrich et al. |
| 6,671,563 B1 | 12/2003 | Engelson et al. |
| 6,779,024 B2 | 8/2004 | DeLaHuerga |
| 6,897,780 B2 | 5/2005 | Ulrich et al. |
| 7,165,221 B2 * | 1/2007 | Monteleone et al. ........ 715/738 |
| 7,287,290 B2 | 10/2007 | Romano et al. |
| 2001/0032195 A1 | 10/2001 | Graichen et al. |
| 2001/0050610 A1 | 12/2001 | Gelston |
| 2002/0013714 A1 * | 1/2002 | Dubler et al. ................ 705/2 |
| 2002/0072911 A1 * | 6/2002 | Kilgore et al. .............. 704/270 |
| 2002/0158919 A1 | 10/2002 | Nacey |
| 2003/0074222 A1 | 4/2003 | Rosow et al. |
| 2003/0078810 A1 | 4/2003 | Cole |
| 2003/0078811 A1 | 4/2003 | Cole |
| 2004/0243446 A1 | 12/2004 | Wyatt |
| 2005/0010441 A1 | 1/2005 | Wheeler |
| 2005/0219059 A1 | 10/2005 | Ulrich et al. |
| 2005/0283382 A1 | 12/2005 | Donoghue et al. |
| 2006/0004605 A1 | 1/2006 | Donoghue et al. |
| 2006/0114888 A1 | 6/2006 | Schuman |
| 2006/0143045 A1 | 6/2006 | Nacey |
| 2006/0247948 A1 | 11/2006 | Ellis et al. |
| 2007/0004971 A1 | 1/2007 | Riley et al. |
| 2007/0010719 A1 | 1/2007 | Huster et al. |
| 2007/0094045 A1 | 4/2007 | Cobbs |
| 2007/0094046 A1 | 4/2007 | Cobbs |
| 2007/0210917 A1 | 9/2007 | Collins, Jr. et al. |
| 2007/0247310 A1 | 10/2007 | Ulrich et al. |
| 2008/0065430 A1 | 3/2008 | Rosow et al. |
| 2008/0065431 A1 | 3/2008 | Rosow et al. |
| 2008/0065432 A1 | 3/2008 | Rosow et al. |
| 2008/0065433 A1 | 3/2008 | Rosow et al. |
| 2008/0065434 A1 | 3/2008 | Rosow et al. |

* cited by examiner

STEP ①: ENTER PATIENT CRITERIA

PATIENT CRITERIA | ADVANCED OPTIONS

LAST NAME | FIRST NAME

DOB | PID

SEX
- ⦿ DON'T CARE
- ○ MALE
- ○ FEMALE

SERVICE
- DON'T CARE
- MEDICINE
- CARDIOLOGY
- CARDIOTHORACIC SURGERY
- GENERAL SURGERY

SOURCE
- DON'T CARE
- ED
- SDA MED
- SDA SURG
- OR

PREADMITS [TODAY] THROUGH [TODAY]

PATIENT STATUS
- ⦿ ANY STATUS
- ○ PLACEMENT REQUESTED BY KATHY, NOT YET ACCEPTED
- ○ PLACEMENT REQUESTED BY ALL, NOT YET ACCEPTED

🔍 UPDATE LIST >>

CLICK HERE IF THE PATIENT ISN'T FOUND

👥 ADD A PATIENT

STEP ②: SELECT PATIENT

| | LAST NAME | FIRST NAME | DOB | MR # |
|---|---|---|---|---|
| 1 | FIELDS | SALLY | 04/30/56 | 2645836 |
| 2 | FINKLEHOFFER | SALLY | 04/29/68 | 2153956 |
| 3 | JOHNSON | SAMUEL | 09/22/44 | 2956734 |
| 4 | JONES | GERALD | 03/12/75 | 2648596 |
| 5 | MARINO | JEFFREY | 11/12/67 | 2134589 |
| 6 | MOREHOUSE | PAUL | 12/21/67 | 2134946 |
| 7 | SMITH | GERALD | 05/13/68 | 2456983 |
| 8 | THIM | KAY | 01/25/55 | 2453857 |

PATIENT DETAILS | MORE PATIENT DETAILS

MOREHOUSE, PAUL, MALE, MR# 2134946, 12/21/67, DR. ADAM, INTESTINAL PAIN

STEP ③: CLICK NEXT TO LOCATE A BED FOR THIS PATIENT

NEXT >>

FIG. 2

PLACE A PATIENT – FIND BED

STEP ①: ENTER BED CRITERIA

BED CRITERIA | ADVANCED OPTIONS

SEX
- ○ DON'T CARE
- ● MALE
- ○ FEMALE

MONITORED?
- ○ DON'T CARE
- ● YES
- ○ NO

PRESSURE?
- ○ DON'T CARE
- ● NEGATIVE
- ○ POSITIVE

BED STATUS
- ○ DON'T CARE
- ● UNOCCUPIED
- ○ OCCUPIED

TRIAGE
- ● DON'T CARE
- ○ BUMPABLE

SERVICE
- DON'T CARE
- MEDICINE
- CARDIOLOGY
- CARDIOTHORACIC SURGERY
- GENERAL SURGERY
- ORTHO/NEURO/TRAUMA
- WOMEN'S HEALTH
- OUTPATIENT/HOLDING

CARE LEVEL
- DON'T CARE
- ICU
- STEP-DOWN
- GENERAL

UNIT
- DON'T CARE
- C12
- B5E
- N12
- CB5
- CB4

PENDING DISCHARGES
NOW [ ] PLUS [12 HOURS]

🔍 UPDATE LIST >>

STEP ②: SELECT A BED

LIST BY ● BED ○ UNIT

| | UNIT | BED | GENDER | PRIVATE | MONITORED | NEG |
|---|------|-----|--------|---------|-----------|-----|
| 1 | C10  | 1   | MALE   | YES     | YES       | YES |
| 2 | C10  | 2   | –      | NO      | YES       | NO  |
| 3 | B10E | 1   | MALE   | YES     | YES       | YES |
| 4 | B10E | 2   | –      | NO      | YES       | NO  |
| 5 | N10  | 1   | MALE   | YES     | YES       | YES |
| 6 | N10  | 2   | –      | NO      | YES       | NO  |
| 7 | B10I | 1   | MALE   | YES     | YES       | YES |
| 8 | B10I | 2   | –      | NO      | YES       | NO  |

DETAILS OF PATIENT IN BED | MORE BED DETAILS

BED DETAILS
BED IN B10E, NEGATIVE PRESSURE, NEAR NURSE STATION, MONITORED, UNOCCUPIED, NOTES: [NONE]

STEP ③: SELECT AN OPTION

REQUEST BED [B10E,1]
REQUEST UNIT

← BACK   × CANCEL

THIS IS THE PATIENT YOU ARE PLACING:
MOREHOUSE, PAUL, MALE, MR# 2134946, 12/21/67, DR. ADAM, INTESTINAL PAIN

FIG. 3

ENTERPRISE-WIDE HOSPITAL BED MANAGEMENT DASHBOARD SYSTEM

CROSS-REFERENCE TO RELATED APPLICATIONS

The present application is a U.S. continuation patent application of, and claims priority under 35 U.S.C. §120 to, U.S. nonprovisional patent application Ser. No. 10/238,427, filed Sep. 9, 2002, which '427 application is incorporated by reference herein and which '427 application is a nonprovisional patent application of, and claims priority under 35 U.S.C. §119(e) to, U.S. provisional patent application Ser. No. 60/317,784, filed on Sep. 7, 2001, which '784 application is incorporated by reference herein.

FIELD OF INVENTION

The present invention generally relates to the fields of automated resource management and virtual instrument technology. More particularly, the present invention relates to a real-time decision support tool for patient bed assignments and for profiling historical, current and future census levels.

BACKGROUND OF INVENTION

Most hospitals employ an Admission/Discharge/Transfer (ADT) system for managing ancillary information, such as admissions, discharge and transfer data about its patients. However, there are existing problems in ADT systems. One problem, for example, is the inability of current ADT systems to provide sufficient clinical information for appropriate patient placement.

Another problem area is the lack of accurate bed availability information. This generally results in lost admissions and excessive wait times.

Inefficient communication while searching for the appropriate bed for a patient, is another problem.

High incidences of 'observation' outpatients that occupy inpatient beds without payer authorization, is another problem.

A final problem area with current ADT systems is the difficulty in accessing meaningful historical, current and predictive hospital data.

SUMMARY OF INVENTION

The present invention satisfies, to a great extent, the foregoing and other needs not currently satisfied by existing bed management systems. This result is achieved, in an exemplary embodiment, by providing an integrated health care delivery network with enabling technology to maximize bed resources, manage varying census levels, and avoid patient diversions through real-time monitoring, automation and communication.

Preferably, the present invention is embodied in a bed management/census control dashboard (BMD) system that interfaces with and complements existing Admission/Discharge/Transfer (ADT) systems. The BMD system is an easy-to-use business intelligence application that is designed to allow administrators, clinicians and managers to easily access, analyze and display real-time patient and bed availability information from ancillary information systems, databases and spreadsheets. In other words, it enables users to see trends and relationships in hospital management data directly from their desktop personal computers.

The present invention improves patient placement efficiency and saves time and money by assisting with the clinical and business decision process that occurs when a patient needs to be admitted to a hospital, for instance. The dashboard's suite of virtual instruments provides a cross-functional view of enterprise status throughout the organization. Decision makers can easily move from big-picture analyses to transaction-level details while, at the same time, safely sharing this information throughout the enterprise to derive knowledge and make timely, data-driven decisions.

The system of the present invention enables more efficient patient placement by, for example, reducing/eliminating telephone calls and paper processes, and automatically matching patient requirements to available resources. In addition, it is an extremely powerful data warehouse and data mining tool that provides on-demand historical, real-time and predictive reports, alerts and recommendations.

The system of the present invention is real-time and mission critical. That is, it handles both scheduled and emergency events. The system also assists with the clinical and business decision processes that occur when a patient needs to be assigned to a specific bed location, for example.

Collectively, the system provides organizations or enterprises with an array of enabling technologies to: schedule/reserve/request patient bed assignments; assign/transfer patients from an emergency department and/or other clinical areas; reduce/eliminate dependency on telephone calls to communicate patient and bed requirements; apply statistical process control (SPC) and "Six Sigma" methodologies to manage occupancy and patient diversion; and provide administrators, managers and caregivers with accurate and on-demand reports and automatic alerts such as through pagers, electronic mail, telephone and intelligent software agents.

Further features of the present invention include: easy-to-use visual navigation; intuitive interactive interface; easy queries; runs on standard computers; real-time, historical and predictive analyses; user configurable settings; remote access and control; geographical information system interfaces; text-to-speech conversion; interactive agent support and alarms; automatic messaging via email, pagers, telephone, etc.; integrated online help; file management and configuration utilities.

In addition to these features, the system of the present invention is designed to protect patient confidentiality and be fully compliant with the evolving Health Insurance Portability and Accountability Act (HIPAA) regulations. A full security system is embedded within the dashboard to authenticate users, audit user access and assign users to definable system roles. These roles restrict both processes and the ability to view or change key data.

In a preferred embodiment, the system of the present invention is accessible via a web browser or a client application. The supporting architecture of the BMD system is preferably a standard N-tier server based system comprising one or more of the following, depending on user needs: web server, application server, database server and an ADT interface server.

The system comprises several modules that communicates in a fashion to accomplish the advantages and features of the invention. Preferably, the system include a bed placement, ADT interface, data import/export, security communications, communications notification, integrated data mining and reporting, utility and configuration, and/or a login authentication module.

The integrated mining and report module is responsible for preparing in real-time one or more reports that take advantage of the data warehousing capabilities of the BMD system. These reports include, but are not limited to, all varieties of historical census reports, (real-time) census reports, bed manager reports, physician discharge reports, discharge compliance reports, etc.

The utility and configuration module is generally responsible for providing operational functions that allow system operators or users to configure the system as desired. For example, this module allows system operators to add new users, modify new or existing user security settings, add/delete/modify services, units, rooms, beds, floor plan diagrams and the like, including their inter-relationships.

The embedded backup utility module comprises a local version of the bed management database that is constantly updated. Access to this database gives users a self-contained and mobile version of the BMD system that can be used in the event of catastrophic failure of the system or network hardware. Access to this database also provides protection, for example, in the event a hospital crisis removes users from direct access to the hospital's network. The login authentication module is responsible for authenticating or validating a user's login (or other) information. In one instance, this module is configurable to access a hospital's central user login repository to validate a user's login information.

The login authentication module also enables single-user sign-on capability by providing a user with the same username and password used by other applications that authenticates the user with a central user log-in repository.

With these and other advantages and features of the invention that may become hereinafter apparent, the nature of the invention may be more clearly understood by reference to the following detailed description of the invention and to the several drawings attached herein.

BRIEF DESCRIPTION OF PREFERRED EMBODIMENTS

FIG. 2 is an exemplary screen shot used to request a bed for a patient.

FIG. 3 is an exemplary screen shot used to locate a specific bed or unit for a patient.

DETAILED DESCRIPTION OF PREFERRED EMBODIMENTS

Figure 1:
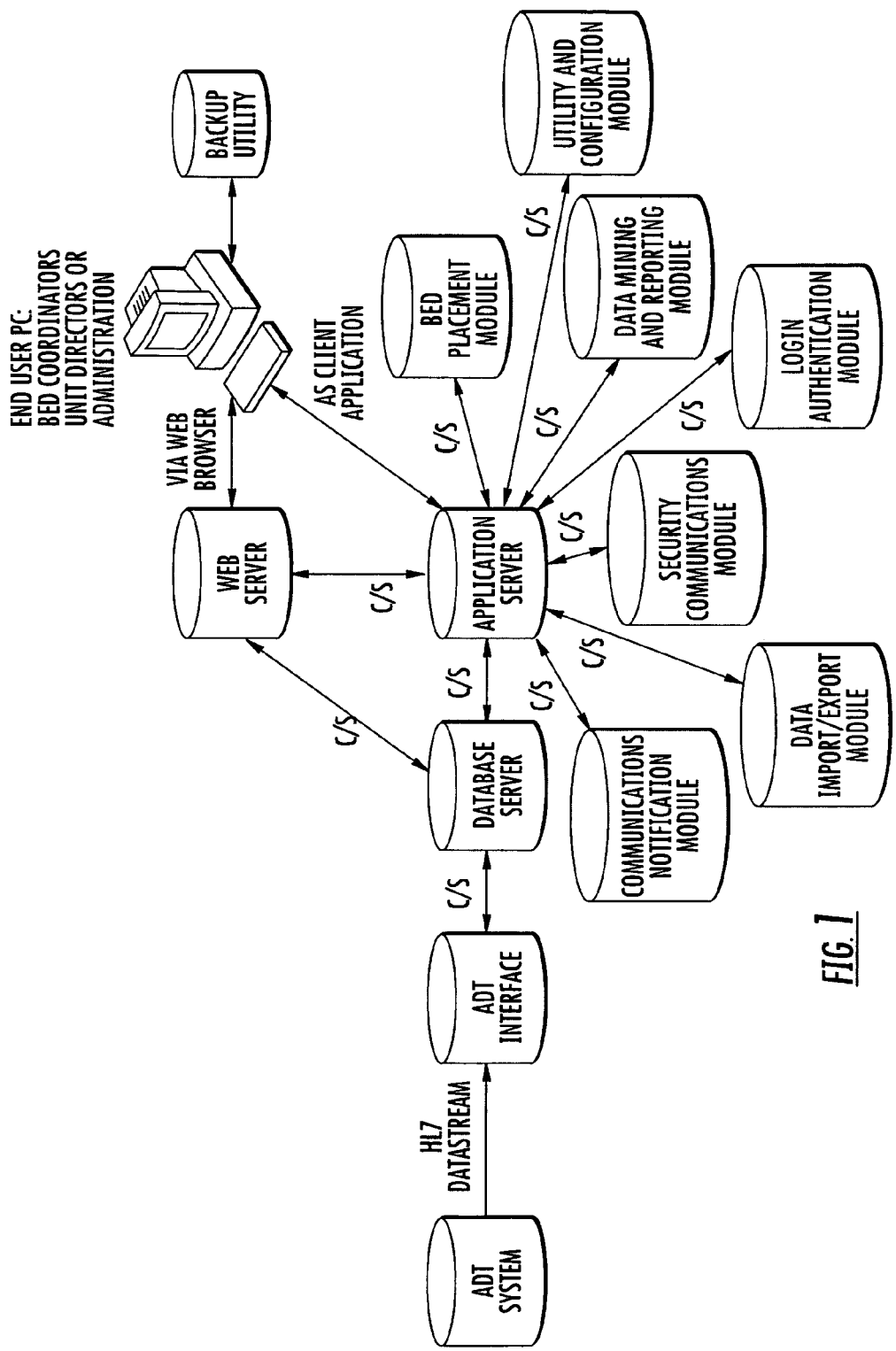
FIG. 1 is a system diagram of the components of the ) bed management dashboard system in accordance with a preferred embodiment of the present invention.

Referring now to the drawings, in FIG. 1 there is shown a system diagram of the components of the present invention, and the information flow from the ADT system to a user's desktop.

In the embodiment depicted, the major components include an ADT interface, database server, an application server, web server, and an end-user application. One or more modules can be added to the system to meet an end user's needs. These modules communicate directly with the application server and provide a user with different, unique and independent functionality.

The BMD system of the present invention is designed to interface with any ADT system that provides a Health Level 7 (HL7) interface. HL7 is an industry standard data format for health-related information.

Referring now to FIG. 1, key information from a hospital's ADT system is automatically fed to the bed management dashboard system of the present invention via a health level seven (HL7) data stream, for example. In a large hospital, the bed management dashboard (BMD) system of the present invention is capable of receiving 12,000 or more transaction messages a day. These messages are parsed into appropriate data elements by the HL7 parser and are stored on a database server. A client application preferably runs on an end-user's desktop and/or a wireless messaging server or PDA.

As shown in FIG. 1, the end users may be bed coordinators, unit directors or administration officials. The client application is preferably a client-server application. Alternatively and optionally, the client application may run via a web browser. Also, the BMD system preferably employs software technology, such as ActiveX, to authenticate user logins across a hospital's network. This approach enables organizations and end users to have a 'single-user sign-on' solution to authenticate qualified personnel and grant access to the BMD system.

An important feature of the BMD system of the present invention is that it re-formats information from the ADT system and presents it to the user in a very user-friendly and process-efficient manner. Dynamic and interactive graphical presentations of data are used extensively.

FIG. 2 illustrates how all the patients from a given admitting source, such as an Emergency Department, is displayed and selected from a dynamically sortable Smart Table. It is embodied in an exemplary screen shot that is primarily used to specify a patient.

Referring to the three major steps shown in FIG. 2, the user first enters various criteria to identify the patient. These criteria include the patients, last name, first name, date of birth or personal identification number, for example. The criteria may also be of a general nature, such as by patient status, pre-admits through a desired time period, or the type of medical service. General search criteria may produce a plurality of patients.

The system then displays all of the patients meeting the specified criteria. Finally, the user selects the patient in question and presses the NEXT button to move to another screen, where an available bed is located and requested.

Noteworthy is the fact that hospital beds are classified as having pre-defined attributes, such as being 'monitored' or being assigned to the 'surgery' service.

The needs of patients are similarly described with attributes, such as 'monitor required' or 'scheduled for surgery'.

As illustrated in FIG. 3, the BMD system of the present invention helps to find those available beds in the hospital that meet the specific needs of a patient by guiding the clinical staff through a set of process screens that perform the match. Once a patient is selected, the exemplary 'Bed Finder' screen of FIG. 3 is used to locate a specific bed or unit for the patient. In the embodiment depicted, the user first enters various criteria about the type of bed that is needed, such as patient gender, whether monitoring required, the level of care required, and the like. The system then displays all of the available beds that meet the specified criteria. The Bed Finder screen also displays information about the patient for which a bed is being sought. Finally, the user selects a particular bed for the previously specified patient.

Decisions for patient placement may be centralized or de-centralized. In either scenario, the BMD system of the present invention allows proper communication between the affected parties or users. Status of decisions is automatically tracked, and a monitoring process is capable of detecting and notifying key stakeholders of any process delays. For example, Admitting or Emergency Departments can be automatically notified of decisions, if appropriate.

Figure 4:
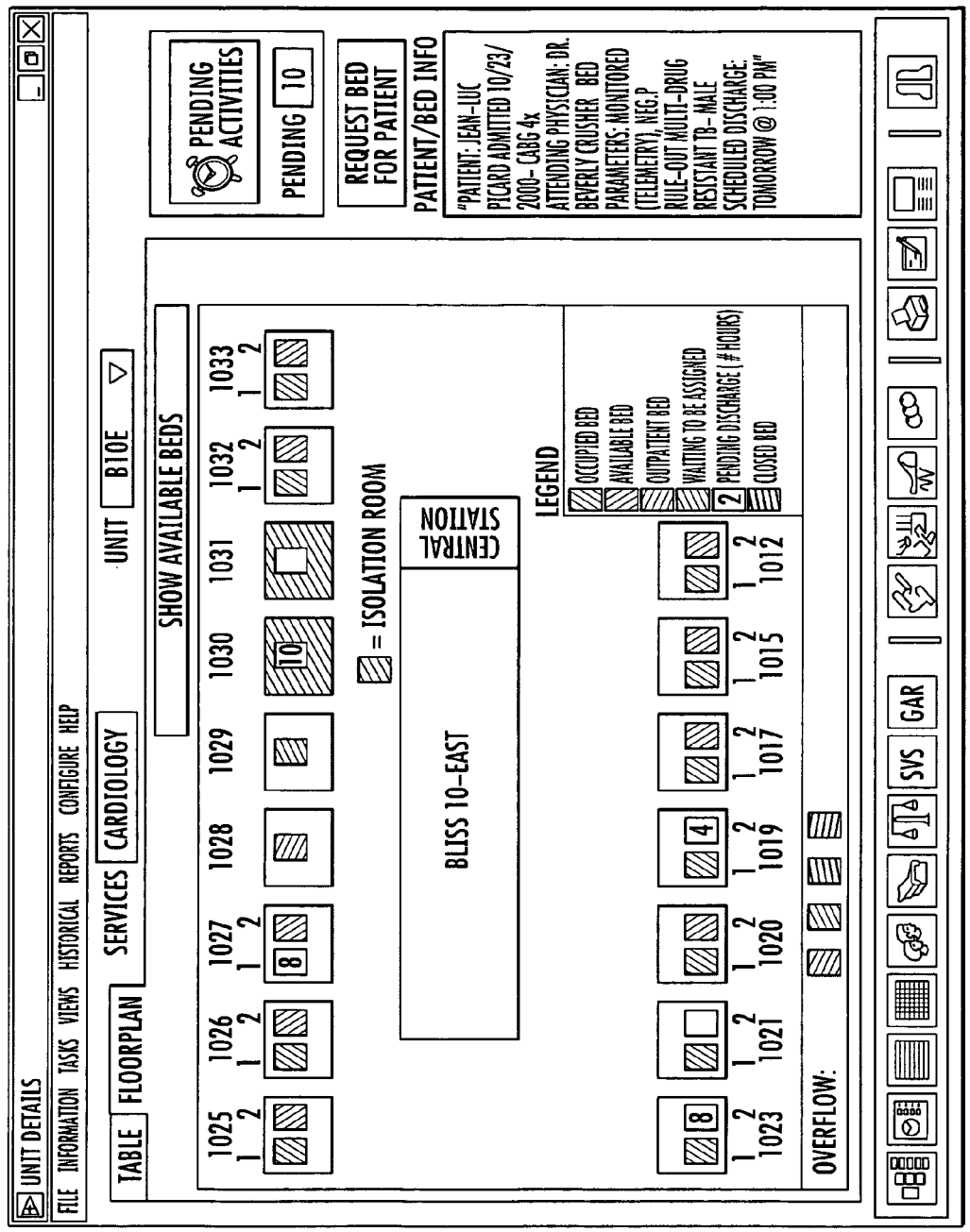
FIG. 4 is a graphical view of an intensive care unit.

Reporting of information is provided by online screen views of data tailored to the needs of a particular class of system user. FIG. 4 illustrates an exemplary embodiment of how patient information can be viewed in a dynamic and interactive floor plan mode.

In the embodiment depicted, there is shown a customized graphical view of an intensive care unit. Each bed is presented as a square using a simplified floor plan view. In a preferred embodiment, colors are used to indicate the selected attribute of the patient or bed. For example, the display in FIG. 4 may be configured to show available beds in green and occupied beds in red. Flashing gray beds may represent beds with pending discharges. Closed or inactive beds may be color-coded black. Many other color-coded options are available via a pull-down selector. These include patient and bed attributes such as gender, monitored bed, negative pressure room, and type of medical service (i.e. cardiology, surgery/orthopedics, etc.).

In addition, each bed icon can also display a numeric value indicating how many hours remain until a patient is scheduled to be transferred or discharged. Conversely, these numeric indicators can also indicate how long a patient has been in a given bed. This feature is important in that hospitals typically do not have an outpatient remain in 'outpatient' status for longer than 23 hours. The BMD system can effectively alert (via flashing icons, audible alarms, email, pager, telephone call, etc.) the appropriate personnel when the 23-hour threshold has been reached.

Unit personnel can view both detailed information as well as summary roll-ups of their patients. Administrators, program directors and the like, may view data over a wider scope that encompasses multiple units, services or physicians, for example. Longer-term, retrospective reporting is also supported, both by user-configured screen-based summaries, as well as by third party tools, such as Crystal Reports, via a link, such as an OBDC link, to the database.

Figure 5:
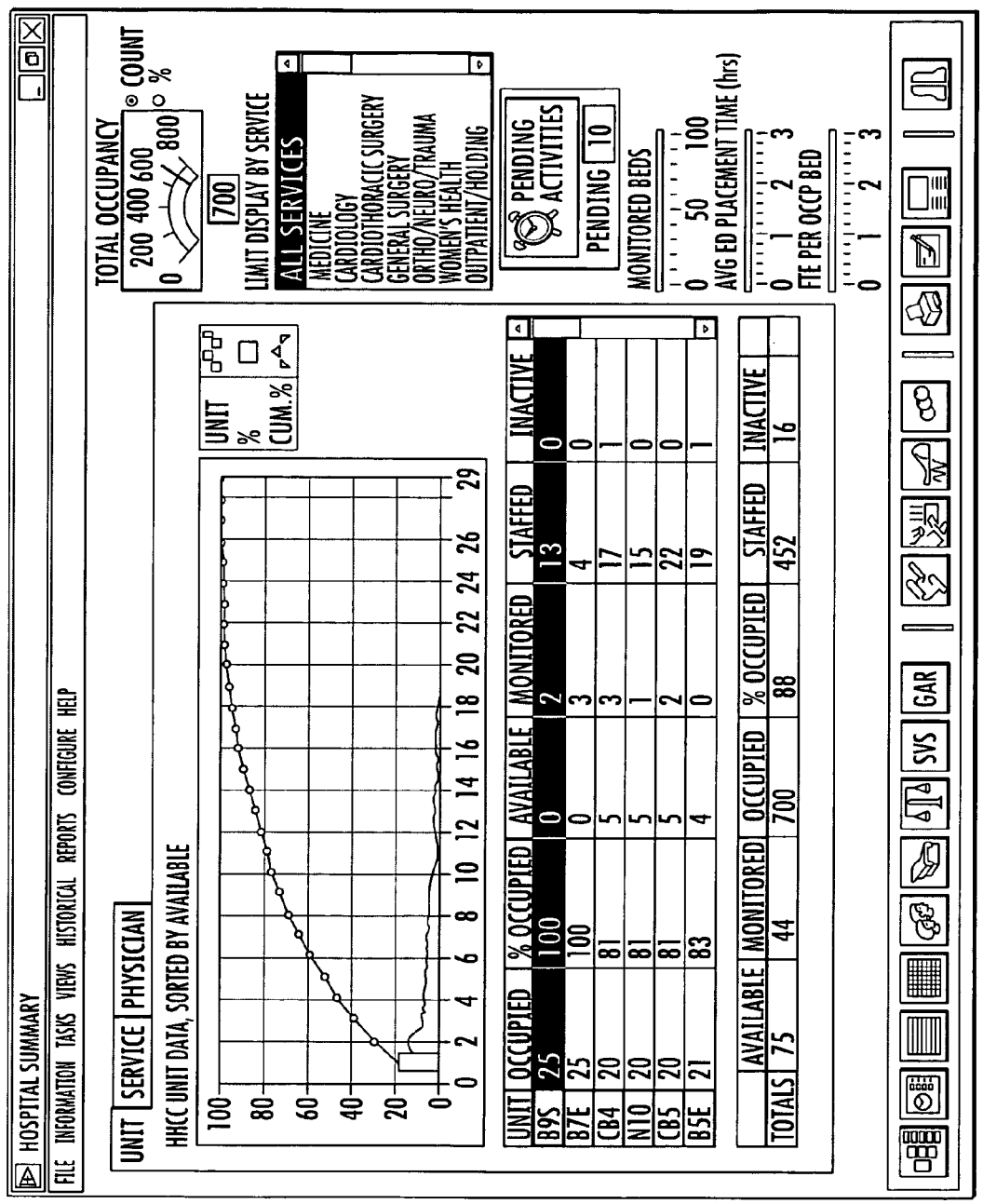
FIG. 5 is an exemplary screen shot of a hospital summary report.

An example of a summary report is shown in FIG. 5. Administrators who need to see a global view of the hospital status primarily use this exemplary screen shot. The system's embedded report engine uses Statistical Process Control (SPC) tools, including Control and Run Charts, Pareto Analysis and Multi-parameter Analysis, when appropriate. This module is particularly useful for monitoring and analyzing parameters in real time, such as patient occupancy and throughput, referral and payment patterns and network activity.

For example, table and Pareto charts can be used to profile the various units and the current status summaries of each unit. These patients can also be rolled up into services, or grouped by physician. In addition, patients can be aggregated in many other ways, such as by time of admission, length of stay, admitting diagnosis, and so forth.

Further, each of the screens depicted in FIGS. 2 through 5 contains button features along the bottom of the screen for features such as printing, and for navigating to various modules (i.e., Unit Details, Place Patient, Find Bed, etc.)

A key feature of the BMD system of the present invention is its use of 'Intelligent Agents' to provide assistance and alert the user of important alarm conditions that may otherwise go unnoticed. These agents can be configured to provide notification in the form of on-screen messages, using technology such as Microsoft's Merlin MSAgent™ shown in FIG. 6, or via electronic notification (i.e. emails), pagers, facsimiles, synthesized voice phone messaging, and/or the like.

Figure 6:
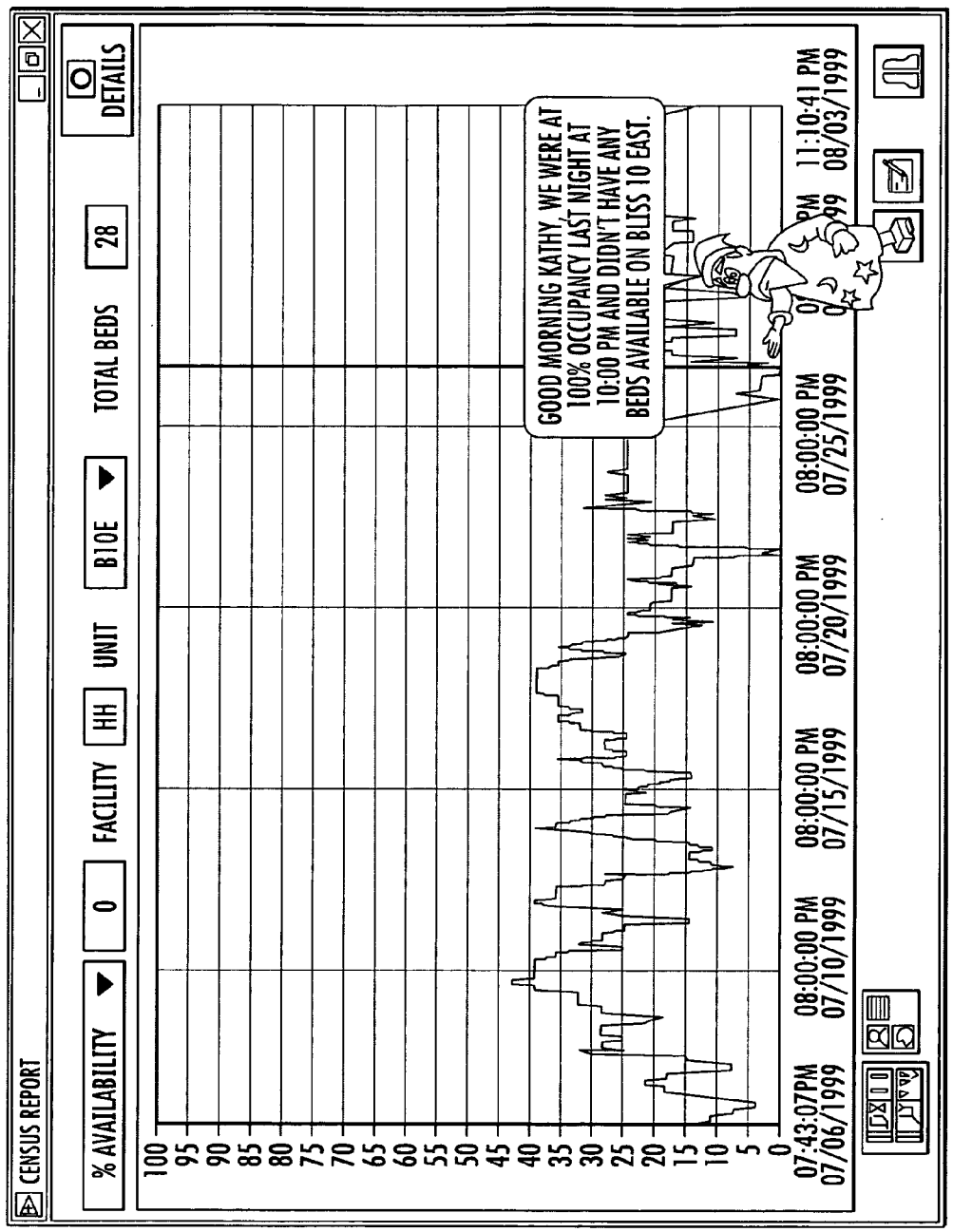
FIG. 6 is an exemplary screen shot of an online agent, which monitors and analyzes data.

These online agents, as depicted in FIG. 6, are constantly monitoring and analyzing patient and census information. They have the ability to detect key system situations, such as a high census in a unit (i.e. no available beds), excessive Emergency Department placement time for a particular patient, or delays in responses to placement requests.

In addition, a full security system is embedded within the BMD system in order to audit user access and to allow users to be assigned definable system roles. In a preferred embodiment, these roles restrict both processes and the ability to view or change key data. The ability to limit roll access to certain data values only of hospital unit and hospital service, enhances patient information privacy. Further, the BMD system is designed to be fully compliant with the Health Insurance Portability and Accountability Act (HIPAA) regulations.

It should be readily recognized that the BMD system of the present invention is capable of providing a variety of screens showing one or more additional features not previously discussed. For example, the BMD system can provide pending activity information, where pending admissions and transfers have been officially registered via a hospital's ADT system. The Pending Activity screen shot may show, highlighted in red, for example, requested bed placements or patient transfer requests from units that wish to transfer patients. In a preferred embodiment, the Pending Activity screen may be divided into upper and lower parts, where the top table shows the amount of pending activity coming in, and the bottom table shows the pending activity that is outgoing.

In all cases, the screen can show information for a specific unit, a service, or the entire hospital. The user can also limit the display so that they will see the activity that will happen prospectively, such as within the next 3 hours, 12 hours, 24 hours, etc. Also, the user can see the details of who and when a request was specifically made.

The BMD system of the present invention can also interface with other ancillary information systems such as staffing, "time and attendance" and clinical information systems. This capability allows the BMD system to provide a wide array of multi-dimensional data, such as available (and required) staffing levels to meet occupancy demands, clinical information that may be useful in determining triage plans, and the like.

Another feature that the BMD system is capable of providing is census reports. Census reports are interactive reports that allow the occupancy trends on a specific unit, group of units or the entire hospital, to be examined over a selectable time interval. The pull-down selector provides options of viewing the data as Occupancy, Percent Occupancy, Availability and Percent Availability. A 'data pointer' line can be dragged across the screen report to show the actual numeric value in a field at the top of the report. Additional 'drill-down' details, print and export features are also available.

Another interactive report available from the BMD system of the present invention, is a Physician Discharge Histogram Report. This report rolls up the selected patient discharge activity into a single 24-hour format, for example. Hospital-wide or specific unit data can be selected. Timeframe selection options are also provided. Each histogram bar may represent the number of discharges for a one-hour period of the day. In this instance, the overall bar would display the total for all physicians, while a highlighted sub-bar would represent the value for the specific physician selected in a left-hand text box.

The above description and drawings are only illustrative of preferred embodiments which achieve the features and advantages of the present invention, and it is not intended that the present invention be limited thereto.

By leveraging the power of virtual instrumentation and open architecture standards, the bed management dashboard system of the present invention improves patient placement efficiency and saves time and money by assisting with the clinical and business decision processes associated with patient admissions, transfers and discharges. This integrated technology directly benefits health care providers, payers, and patients.

However, it is also envisioned that the BMD system of the present invention may be useful in applications other than a hospital environment. These applications include, for example, nursing homes, hotels. The applications extend across multi-facility organizations as well by state or other agencies responsible for monitoring access (i.e. intensive care beds available statewide during a natural disaster) and the like. Any modification of the present invention that comes within the spirit and scope of the following claims is considered to be part of the present invention.

What is claimed is:

1. A method for graphically displaying information relating to locations in a health care facility at which patients are placed, comprising the steps of:
   (a) on an ongoing basis, receiving computer-generated transactional messages from one or more computer systems of the health care facility, including a patient admissions/discharge system of the healthcare facility, and automatically updating a database with information extracted from the computer-generated transactional messages, which information pertains to the patients and the locations for patient placement in the health care facility, whereby information about patients and locations for patient placement is maintained on an ongoing basis in the database via continual updates thereto;
   (b) accessing the database and, based thereon, displaying, in a floor plan view, a graphical representation of a plurality of locations for patient placement in the health care environment, which graphical representation visually includes representations of at least a portion of the information about patients and locations for patient placement that is maintained in the database;
   (c) wherein the locations for patient placement include one or more units, rooms, or beds.

2. The method of claim 1, wherein the locations for patient placement, for which information is maintained in the database, include all of the locations for patient placement at the health care facility.

3. The method of claim 1, wherein the locations for patient placement include units of the health care facility, each unit having a plurality of patient beds.

4. The method of claim 1, wherein the locations for patient placement include rooms of the health care facility, each room having at least one patient bed.

5. The method of claim 1, wherein the locations for patient placement include patient beds of the health care facility.

6. The method of claim 1, wherein the information about patients comprises patient attributes.

7. The method of claim 6, wherein the graphical representation includes displaying different colors for conveying information about a particular patient attribute.

8. The method of claim 6, wherein the patient attributes include at least one of: patient name; patient date of birth; patient identification number; patient status; patient gender; symptoms; admitting diagnosis; time of admission; and type of medical service required.

9. The method of claim 1, wherein the information about the locations at the health care facility for patient placement includes bed attributes.

10. The method of claim 9, wherein the graphical representation includes displaying different colors for conveying information about a particular bed attribute.

11. The method of claim 9, wherein the bed attributes include at least one of: bed occupancy status; bed availability status; whether the bed is monitored; and the medical service assigned to the bed.

12. The method of claim 1, wherein at least information about the locations for patient placement is graphically displayed.

13. The method of claim 1, wherein step (b) is performed in connection with providing a graphical user interface through which a suitable location for patient placement of a patient is determined.

14. The method of claim 1, wherein step (b) is performed in connection with providing a graphical user interface through which a location for patient placement of a patient is requested.

15. The method of claim 14, further comprising tracking the status of the bed request and wherein the graphical representation includes displaying different colors for conveying information about the status of the request.

16. The method of claim 15, further comprising notifying a unit of the health care facility of a bed request decision.

17. The method of claim 1, further comprising matching,
   (i) information maintained and updated in the database about locations for patient placement with,
   (ii) information maintained and updated in the database about a particular patient, whereby available locations of the health care facility that are suitable for patient placement of the particular patient are determined.

18. The method of claim 17, wherein step (b) is performed in connection with displaying a graphical user interface through which a suitable location for patient placement of the particular patient is requested.

19. The method of claim 1, wherein step (b) is preformed in connection with the displaying of a graphical user interface through which a suitable location for patient placement of a patient is requested.

20. The method of claim 1, wherein the graphical representation is displayed on screen of a wireless handheld device.

21. The method of claim 1, wherein the graphical representation is displayed within a web browser.

22. The method of claim 1, wherein the graphical representation is displayed on screen of a monitor located at a particular unit of the health care facility, and wherein performance of said step (b) includes displaying only those locations for patient placement that are part of the particular unit of the health care facility.

23. The method of claim 1, wherein the messages are received from an Admission/Discharge/Transfer (ADT) System of the health care facility.

24. The system of claim 1, wherein the graphical representation comprises a floor plan view of a unit of the health care facility, and wherein the graphical representation includes icons each representing a bed of the unit.

25. The system of claim 24, wherein different colors or animation is displayed in order to represent different information about an attribute of the bed represented by the icon.

26. The system of claim 24, wherein different colors or animation is displayed in order to represent different information about a patient placed at the bed represented by the icon.

27. The system of claim 1, wherein the graphical representation includes a visual indication of the number of hours that remain until a patient is scheduled to be transferred or discharged.

28. The system of claim 1, wherein the graphical representation includes a visual indication of pending transfers or discharges.

29. The system of claim 1, further comprising generating an audible alarm when an attribute associated with a patient or a bed reaches a predetermined threshold.

30. The system of claim 1, further comprising generating and sending a notification when an attribute associated with a patient or a bed reaches a predetermined threshold.

\* \* \* \* \*